United States Patent
Imai et al.

(10) Patent No.: US 8,760,638 B2
(45) Date of Patent: Jun. 24, 2014

(54) MATERIAL IDENTIFICATION AND DISCRIMINATION

(75) Inventors: Francisco Imai, Mountain View, CA (US); Siu-Kei Tin, Milpitas, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/592,663

(22) Filed: Aug. 23, 2012

(65) Prior Publication Data

US 2014/0055775 A1 Feb. 27, 2014

(51) Int. Cl.
*G01N 21/00* (2006.01)

(52) U.S. Cl.
USPC .............................. 356/73; 356/32

(58) Field of Classification Search
USPC ......... 356/3, 4.09, 4.1, 24, 25, 28.5, 32–35.5, 356/FOR. 107, 946, 902, 450–460, 900, 356/901, 479, 497, 511, 512, 496, 477, 356/614; 382/154, 141, 152, 181, 218; 702/172

See application file for complete search history.

(56) References Cited

U.S. PATENT DOCUMENTS

| | | | |
|---|---|---|---|
| 6,584,214 | B1 | 6/2003 | Pappu et al. |
| 7,123,363 | B2 | 10/2006 | Puttappa et al. |
| 7,307,734 | B2 | 12/2007 | Dogariu |
| 7,925,056 | B2 | 4/2011 | Presura et al. |
| 2007/0139659 | A1 | 6/2007 | Hwang et al. |
| 2008/0123106 | A1 | 5/2008 | Zeng et al. |
| 2008/0154524 | A1 | 6/2008 | Shirley |
| 2008/0294900 | A1 | 11/2008 | Cowburn |
| 2010/0290053 | A1* | 11/2010 | Robinson ............... 356/451 |
| 2011/0235871 | A1 | 9/2011 | Byren et al. |

OTHER PUBLICATIONS

Shirley et al., "Nonconventional 3D Imaging Using Wavelength-Dependent Speckle", MIT Lincoln Laboratory Journal, vol. 9, No. 2, pp. 153-186, 1996.
Ellis, et al., "Stokes vector correlations and material discrimination from speckle fields" in the Proceedings of SPIE vol. 5432 (SPIE, Bellingham, WA), 2004.
Fujii, et al., "Measurement of surface roughness properties by using image speckle contrast", J. Opt. Soc. Am., vol. 66, No. 11, 1976.
Goodman, "Speckle Phenomena in Optics: Theory and Applications", 2007.
Leonhardt, et al., "Removing ambiguities in surface roughness measurement", Optica Acta, vol. 29, No. 4, 493-499, 1982.
Lu, et al., "Grinding surface roughness measurement based on co-occurrence matrix of speckle pattern texture", Applied Optics, vol. 45, No. 35, 2006.
Haralick et al., "Texture features for image classification", IEEE Trans. Syst. Man. Cybern., vol. 3, 610-621, 1973.
ESPI Brochure "Speckle Pattern Interferometer", 2005.

* cited by examiner

*Primary Examiner* — Tri T Ton
(74) *Attorney, Agent, or Firm* — Fitzpatrick, Cella, Harper & Scinto

(57) ABSTRACT

A material is illuminated with one or more light sources including at least one light source which emits light of controlled coherence properties. Both of a spectral characteristic and a speckle statistic are derived using light reflected from the illuminated material. The spectral characteristic and the speckle statistic are compared against plural entries in a database. Each entry in the database correlates the identity of a material against a corresponding spectral characteristic and a corresponding speckle statistic for the material. At least one candidate for the identity of the illuminated material is determined based at least in part on the comparison.

20 Claims, 15 Drawing Sheets

Polychromatic speckle contrast versus RMS roughness.

Gray level co-occurrence matrix

GLCM energies and the fitted exponential curve.

Ra versus the feature vector ($y_0, k, \sigma$)

Fitting the GLCM energy exponential function

MATERIAL IDENTIFICATION AND DISCRIMINATION

FIELD

The present disclosure relates to material identification and discrimination, and more particularly relates to identifying or discriminating materials based in part on speckle statistics.

BACKGROUND

One area of research beneficial to machine automation concerns automatic identification and discrimination of materials, particularly without contact to the material. For example, in robotic assembly or sorting plants, it can be important to identify materials or parts by optical means based on their material properties for assembling or sorting purposes.

In this context, it has been considered to measure statistics of a speckle pattern, to assist in a non-contact identification of a material or estimation of material properties thereof. A speckle pattern results from interference of light waves scattered by a material when illuminated by a light source (such as a laser) with controlled coherence properties.

SUMMARY

There have been attempts to correlate speckle statistics with surface roughness. In some applications such as quality control of surface finish of metal products, surface roughness is of primary interest. In the field of material identification and discrimination, however, surface roughness is only one of the material properties that may be used to identify and discriminate materials.

More generally, a speckle pattern captures information about the interaction of a material and incident coherent light. Different statistics derived from the speckle pattern may provide different aspects of this interaction that may be used as features for material identification and discrimination. Furthermore, it is known that spectral reflectance of a material can be a discriminative characteristic of the material, especially for a raw or natural material. A combination of speckle and spectral features would then allow identification and discrimination of a diversity of different materials, natural or artificial.

The foregoing situation is addressed by collecting both spectral characteristics and speckle statistics, and comparing the spectral characteristics and speckle statistics against a database that correlates identities of various materials to such statistics.

Thus, in an example embodiment described herein, a material is illuminated with one or more light sources including at least one light source which emits light of controlled coherence properties. Both of a spectral characteristic and a speckle statistic are derived using light reflected from the illuminated material. The spectral characteristic and the speckle statistic are compared against plural entries in a database. Each entry in the database correlates the identity of a material against a corresponding spectral characteristic and a corresponding speckle statistic for the material. At least one candidate for the identity of the illuminated material is determined based at least in part on the comparison.

By comparing both spectral characteristics and speckle statistics against a database, it is ordinarily possible to perform a more robust discrimination between materials, including materials which might have similar surface roughness, similar spectral reflectance or other similarities.

In further aspects of some representative embodiments, the one or more light sources may include multiple coherent light sources, each comprised of a laser with a respectively different wavelength, or may include at least one incoherent light in conjunction with a laser light source. The light sources may be applied simultaneously or sequentially. Spectral analysis may include capture of light reflected from the illuminated material with a spectral sensor such as a spectral imager or spectrophotometer.

The derived speckle statistic may be different in different embodiments, and analysis may vary depending on the nature of the derived speckle statistic. For example, the speckle statistic may comprise a speckle contrast, monochromatic contrast or polychromatic contrast. The speckle statistic may also comprise a wavelength correlation between a first and second speckle fields captured from coherent light sources with respectively different wavelengths, and analysis may comprise cross-correlation of first and second speckle fields. The speckle statistic may also comprise an angle correlation between a first and second speckle fields captured from coherently illuminating the material at different illumination angles, and analysis may comprise cross-correlation of the first and second speckle fields. Likewise, the speckle statistic may comprise a gray level co-occurrence matrix (GLCM), or a digital counts per second (DCPS), or a skewness or kurtosis defined respectively by the standard 3rd or 4th statistical moment, or a speckle patch size. It is further possible to derive more than a single speckle statistic, such as combinations of more than one of the speckle statistics mentioned above, and to obtain more accurate material discrimination or property estimation through use of such combinations.

This brief summary has been provided so that the nature of this disclosure may be understood quickly. A more complete understanding can be obtained by reference to the following detailed description and to the attached drawings.

DETAILED DESCRIPTION

Figure 1A:
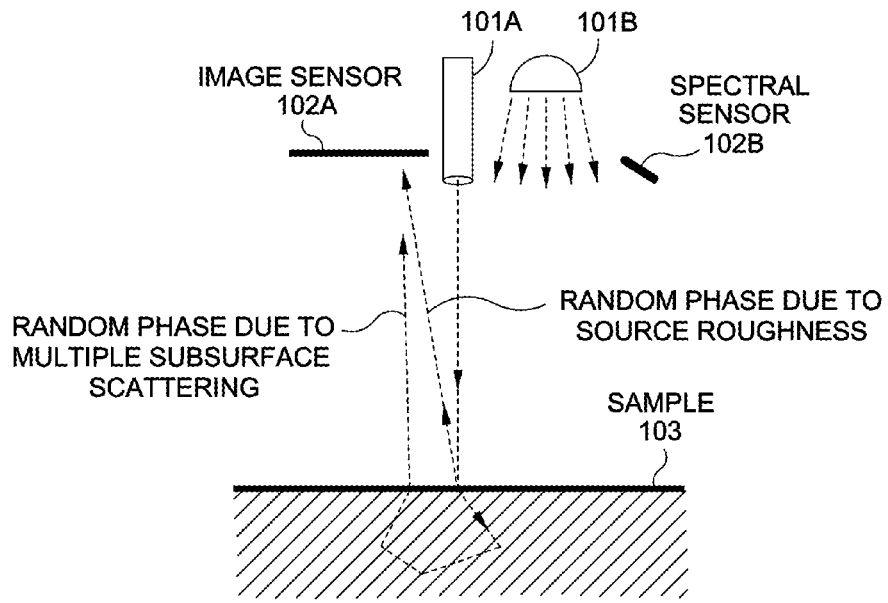
FIGS. 1A to 1G are views for explaining a material identification device according to example embodiments.
Figure 1B:
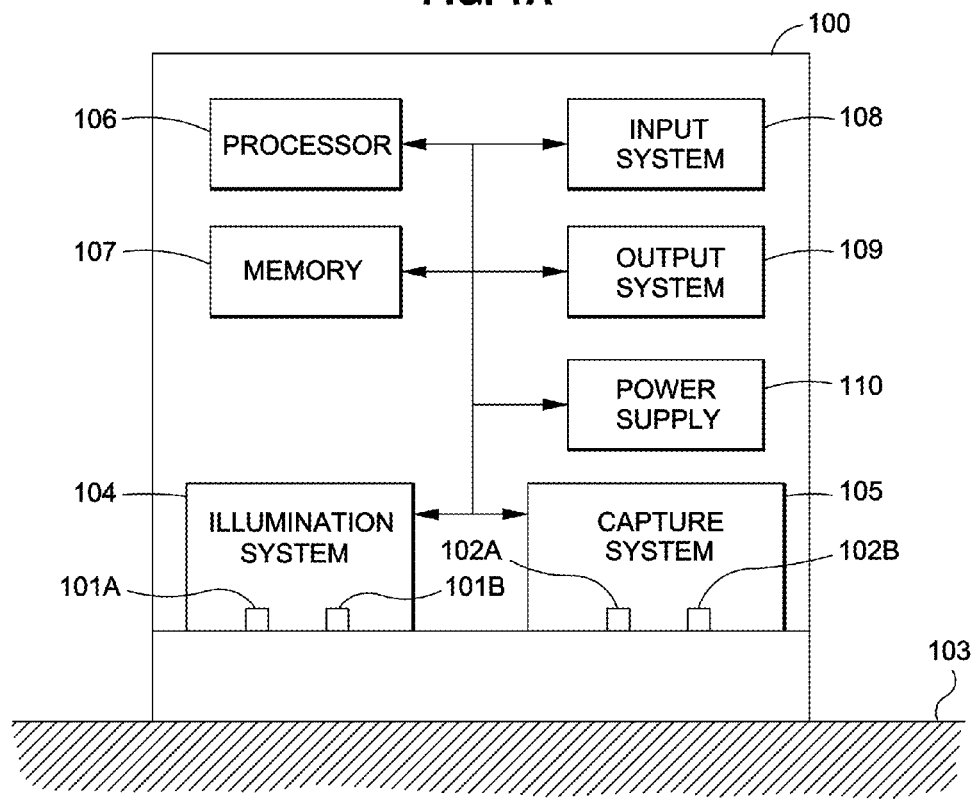

FIGS. 1A and 1B are views for explaining a material identification device for identifying a material using spectral characteristics and speckle statistics.

In particular, FIGS. 1A and 1B are views for explaining a device which illuminates a material with at least one light source which emits light of controlled coherence properties. The device measures resultant speckle patterns formed on one or more sensors and analyzes the spectral response of the illuminated material.

In the simplified view shown in FIG. 1A, light sources 101A and 101B illuminate a material 103. In particular, light source 101A emits light beams of controlled coherence properties. Image sensor 102A records one or more speckle field images reflected from the illuminated material, whereas spectral sensor 102B records the spectral radiance of light reflected from the illuminated material for subsequent spectral analysis. Material 103 may comprise, for example, a translucent material such as skin tissue, or a material to be sorted such as a recyclable material.

FIG. 1B is a view of an identification device 100 for identifying the material 103 as shown in FIG. 1A. In that regard, identification device 100 is shown in FIG. 1B as a device which is placed on or near to material 103, but it should be understood that identification device 100 might be embodied in other arrangements and with other positioning relative to material 103. For example, identification device 100 could be arranged in other housings or devices which include a laser emitter and sensor as shown in FIG. 1A. In addition, the elements of FIG. 1A or FIG. 1B could be embodied in separate devices or across multiple devices in a system. For example, light sources 101A and 101B and sensors 102A and 102B could be embodied in two or more devices. Furthermore, light sources 101A and 101B could be the same light source, and sensors 102A and 102B could be the same sensor.

As shown in FIG. 1B, identification device 100 includes light sources 101A and 101B, sensors 102A and 102B, illumination system 104, capture system 105, processor 106, memory 107, input system 108, output system 109 and power supply 110.

Light sources 101A and 101B are elements at least one of which emits a light beam with controlled coherence properties. For example, light source 101A might comprise a monochromatic laser beam while light source 101B might comprise an incandescent light source such as a halogen lamp. In some embodiments, light sources 101A and 101B each include a laser light source. Thus, a light source according to the disclosure might comprise multiple coherent light sources each comprised of a laser with a respectively different wavelength. Multiple different light sources, such as light sources 101A and 101B, may be applied simultaneously or sequentially. In other embodiments, a single light source such as a single monochromatic laser might be used.

Speckle patterns are caused by a phenomenon when a material is illuminated by a coherent light such as a laser. An interference pattern is observed from the scattering of the coherent light caused in part by the surface microstructure and in part by the subsurface microstructure of the illuminated material. The speckle pattern may appear to be random, but the statistical properties can be correlated to the surface microstructure and subsurface microstructure properties of the illuminated material.

The light used for the illumination should have some degree of coherence, because the speckle pattern is caused by the interference of the coherent light waves with the material. Coherence may include spatial coherence (e.g., light waves remaining correlated over a long distance, possibly averaged over time) and temporal coherence (e.g., light waves remaining correlated over long time). One example of a light source with spatial and temporal coherence is a monochromatic laser. However, in some embodiments, temporal coherence may not be required.

Image sensor 102A is an image sensor for recording the speckle pattern which results from interference of reflected light waves when material 103 is illuminated with light from light source(s) 101A and/or 101B having controlled coherence properties. Spectral sensor 102B records the spectral radiance of light reflected from the illuminated material. Spectral sensor 102B may comprise, for example, a spectral imager or spectrophotometer. In the case of spectral imager, an image of spectral radiance is recorded, whereas in the case of spectrophotometer, a single measurement is recorded. In some examples, therefore, two images may be captured by sensors 102A and 102B, specifically a speckle field image and a spectral image, each of which can be used to determine properties of material 103.

Illumination system 104 is a system for driving light source(s) 101A and/or 101B to illuminate material 103. In that regard, illumination system 104 might comprise, for example, one or more motors and associated parts for driving light source(s) 101A and/or 101B simultaneously or sequentially.

Capture system 105 is a system for capturing multiple speckle patterns and spectral images respectively created by driving light source(s) 101A and/or 101B to illuminate material 103, for example with different wavelengths or from different angles. Capture system 105 might comprise, for example, one or more motors and associated parts for physically moving sensors 102A and/or 102B so as to record speckle fields and spectral measurements for different incident angles or wavelengths of light, or might comprise multiple ones of sensors 102A and/or 102B to record speckle fields and spectral measurements for different incident angles or wavelengths of light.

Processor 106 a computer processor such as a single core or multi-core central processing unit (CPU) or micro-processing unit (MPU), which is constructed to realize functionality according to the disclosure. Processor 106 might comprise multiple computer processors which are constructed to work together. Processor 106 communicates with the elements of identification device 100 to control the elements to perform required functionality or to obtain required data. For example, processor 106 may control illumination system 104 to illuminate material 103 from different angles, and may control capture system 105 to drive sensors 102A and 102B to record speckle fields and spectral measurements for different incident angles or wavelengths of light.

Memory 107 stores constants, computer-executable programs, and the like for operation of processor 106, including programs for execution of various flowcharts. Memory 107 may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), micro-drive, a read only memory (ROM), random access memory (RAM), erasable programmable read only memory (EPROM), electrically erasable programmable read only memory (EEPROM), dynamic random access memory (DRAM), video RAM (VRAM), a magnetic tape or card, optical card, nanosystem, molecular memory integrated circuit, redundant array of independent disks (RAID), a nonvolatile memory card, a flash memory device, a storage of distributed computing systems and the like.

Figure 3A:
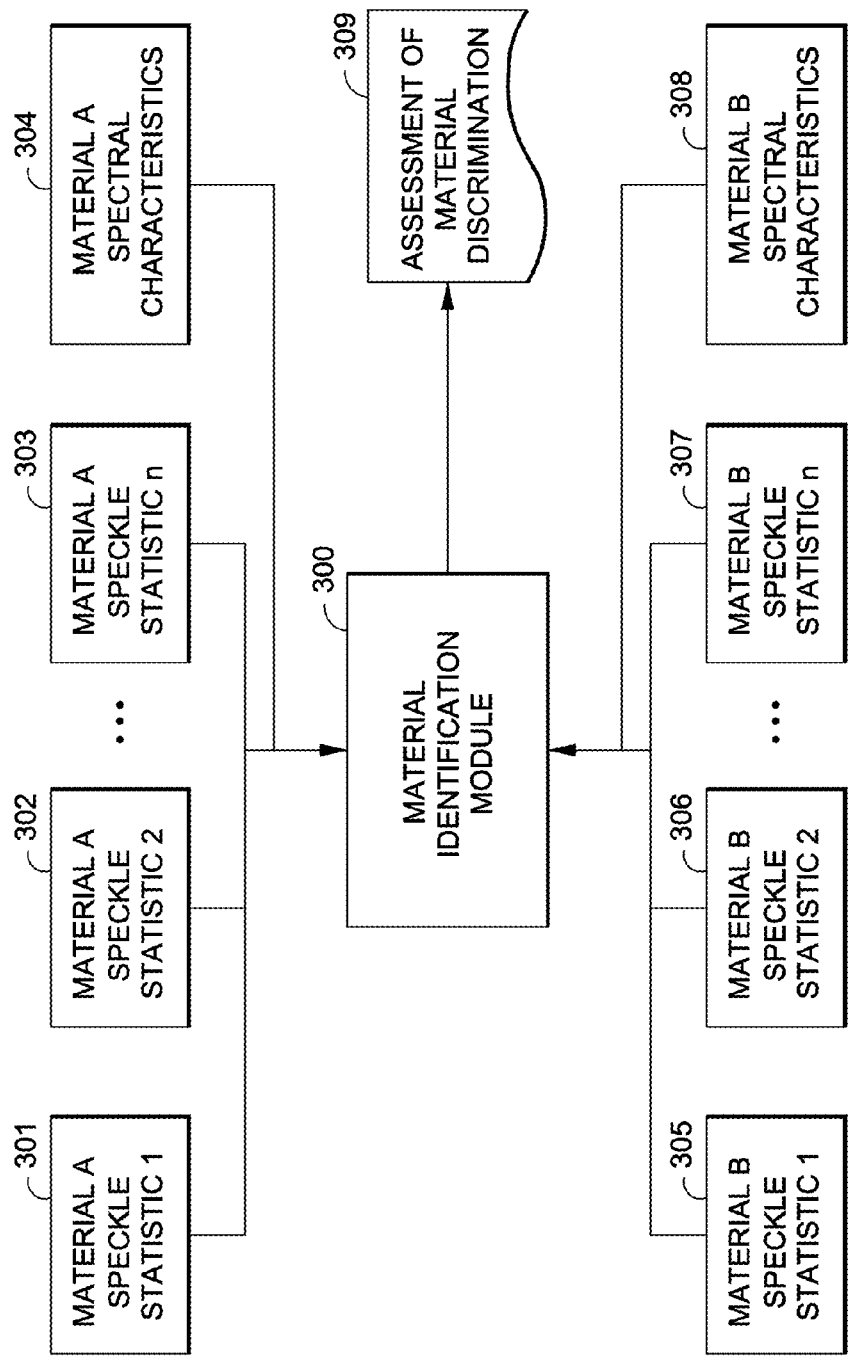
FIGS. 3A and 3B are simplified block diagrams for explaining a material identification module according to an example embodiment.
Figure 3B:
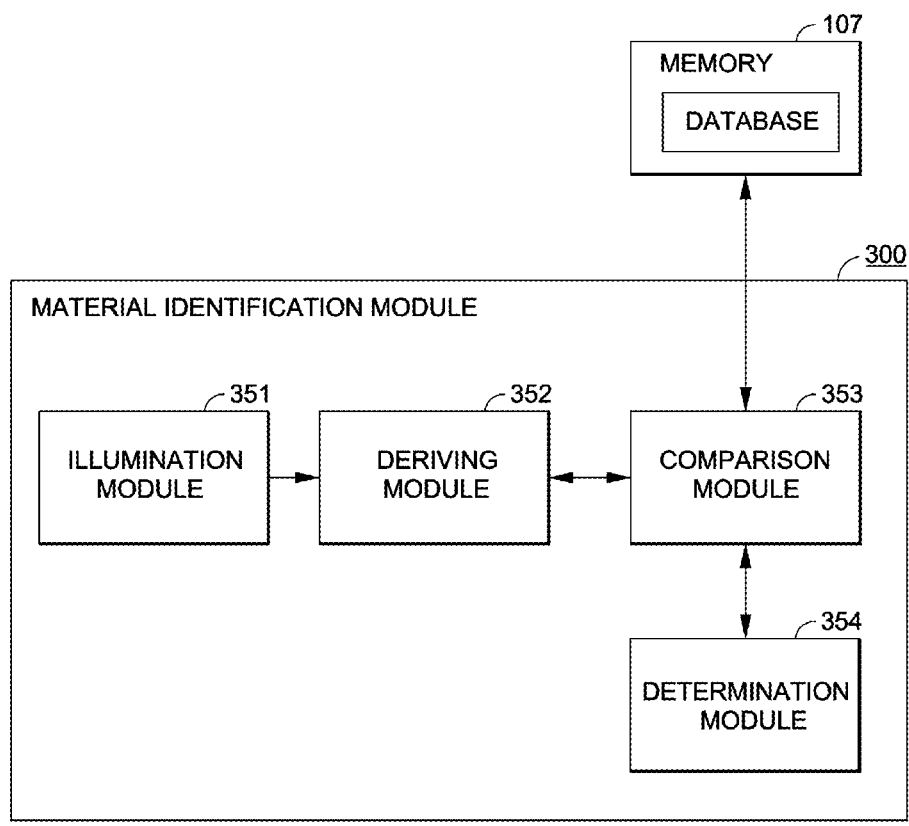

Memory 107 may retrievably store thereon material identification module 300 as described herein and shown in FIG. 3B. According to this example embodiment, the identification module 300 includes at least an illumination module 351 for illuminating the material with one or more light sources including at least one light source which emits light of controlled coherence properties, and a deriving module 352 for deriving both of a spectral characteristic and a speckle statistic. The spectral characteristic and speckle statistic are derived using light reflected from the illuminated material. The material identification module 300 further includes a comparison module 353 for comparing the spectral characteristic and speckle statistic against plural entries in a database. Each entry in the database correlates the identity of a material against a corresponding spectral characteristic and a corresponding speckle statistic for the material. Additionally, the material identification module 300 includes a determination module 354 for determining at least one candidate for the identity of the illuminated material based at least in part on the comparison. In another embodiment, determination module 354 determines not just one candidate, but a probability distribution function of the identity of the illuminated material based at least in part on the comparison, wherein each candidate material identity is associated with a probability.

Input system 108 inputs data such as settings or control parameters for operation of identification device 100. For example, in some example embodiments, it might be useful to input precise control parameters from an external processing device such as a computer. Accordingly, input system 108 may include a connection and associated elements for communicating with other devices.

Output system 109 provides output of data obtained or produced from identification device 100, either to a user, e.g., via a display in output system 109 or via a connection to output data to an external device.

Power supply 110 is a primary power source such as an alkaline battery or a lithium battery, a secondary battery such as a NiCd battery, a NiMH battery or a Li battery, or the like for providing power to identification device 100.

In FIG. 1B, identification device 100 is shown as a standalone device, but other embodiments might involve illumination system 104 and/or capture system 105 in a first housing coupled to remaining components in a second housing, such as by unshown wireless or wired interfaces to a computer.

FIGS. 1C to 1G are views for explaining spectral sensor 102B for capturing spectral information according to example embodiments. These embodiments are shown merely for purposes of example, and other arrangements are possible. For example, in some embodiments image sensor 14 may be constructed to capture high-resolution additional spectral data itself, and thus additional hardware may not be necessary.

Figure 1C:
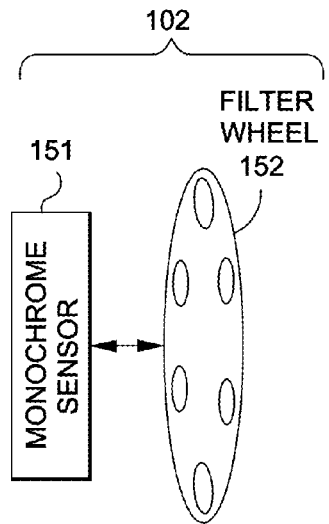
Figure 1D:
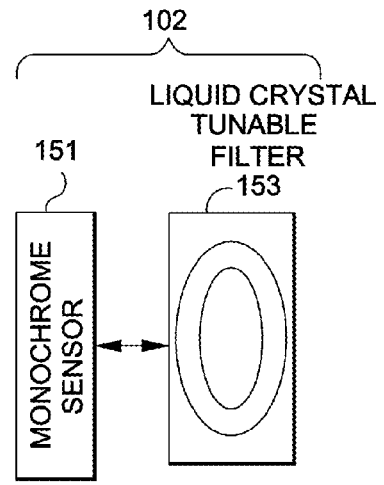

FIGS. 1C and 1D depict embodiments with a monochrome sensor 151 and a set of narrow-band filters. The narrow-band filters, in turn, can be comprised of a filter wheel 152 (FIG. 1C) with filters with different spectral bands, or a liquid crystal tunable filter 153 (FIG. 1D). Either of these embodiments ordinarily provides relatively high spectral resolution and relatively high spatial resolution. However, due to cost and size of the system, such embodiments ordinarily are only appropriate for high-end imaging of static materials, taking into account the imaging capture time needed to move the filter wheel or to capture images using the liquid crystal tunable filter.

Figure 1E:
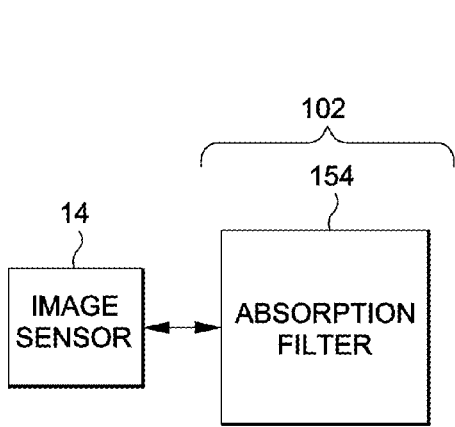

FIG. 1E depicts an embodiment in which image sensor 14 is an RGB sensor combined with an absorption filter 154, for example as shown in U.S. Pat. No. 7,554,586, "System and method for scene image acquisition and spectral estimation using a wide-band multi-channel image capture", the contents of which are incorporated by reference herein. The captured RGB from image sensor 14 without an external filter provides the traditional image capture. Meanwhile, a spectral reflectance estimation process is performed to get higher spectral resolution data from lower spectral resolution captured data provided by the combination of unfiltered images from image sensor 14, and filtered RGB images from absorption filter 154. The external absorption filter 154 changes the overall sensitivities of the original RGB sensor providing three additional channels. This embodiment provides relatively high spatial resolution and is relatively usable for dynamic scenes if the filter 154 is fast-switching, and there is ordinarily no need for a secondary sensor as in the embodiments of FIGS. 1C and 1D. On the other hand, the embodiment of FIG. 1E tends to have relatively low spectral resolution.

Figure 1F:
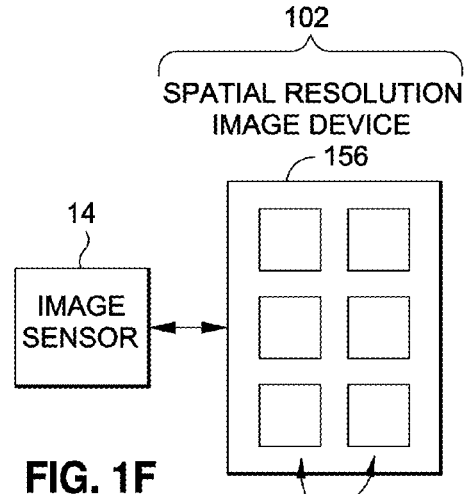

FIG. 1F depicts an embodiment in which image sensor 14 is an RGB sensor combined with an additional high-spectral resolution but low-spatial resolution imaging device 156, for example a device which includes an array of spectral sensing devices 155 with high-spectral resolution such as an array of filters with distinct spectral transmittances, such as described in U.S. Publications No. 2010/0045050, 2010/0046077, 2010/0053755 and 2010/0182598, the contents of which are incorporated by reference herein. Main RGB imaging sensor 14 provides the conventional photography capture, whereas a secondary sensor (array of high-spectral resolution sensors) 155 works as a low-spatial resolution but high-spectral resolution spectral measurement device. The arrangement of FIG. 1F provides high spectral resolution with relatively low cost, and can be applied to dynamic scenes. On the other hand, due to the relatively low resolution of the secondary stage (e.g., the array of spectral sensing devices), this configuration ordinarily has a low spatial resolution.

Figure 1G:
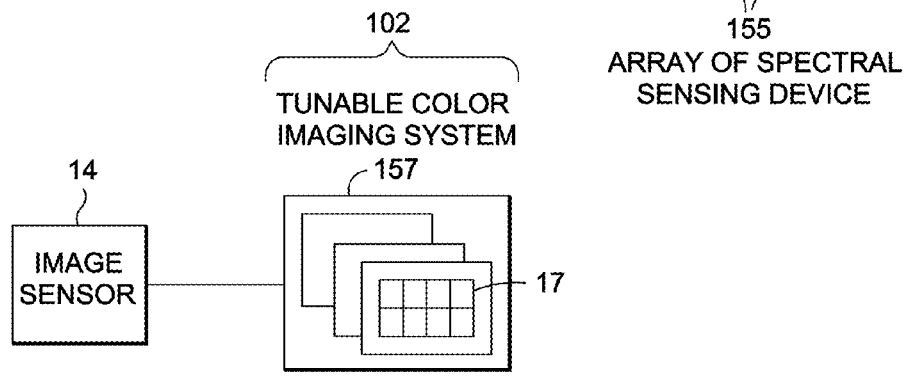

FIG. 1G depicts an example embodiment in which image sensor 14 is an RGB imaging sensor coupled with a color imaging system 157 with tunable spectral sensitivities. The tunable spectral sensitivities may be tunable in accordance with a capture parameter 17. This arrangement is described in detail in U.S. application Ser. No. 12/949,592, by Francisco Imai, entitled "Adaptive Spectral Imaging By Using An Imaging Assembly With Tunable Spectral Sensitivities", the contents of which are incorporated by reference herein.

As mentioned above, image sensor 14 may itself have high spectral resolution and capture additional multi-spectral data. Thus, additional hardware might not be necessary at all, although multiple captures might be needed. U.S. Pat. No. 7,554,586 describes a method for multi-band capture comprised of one or more illuminants which illuminate with a different spectral power distribution. This method allows the recovery of spectral information of the scene and works relatively well for objects with broad spectral characteristics.

In that regard, any of the embodiments above ordinarily will provide enough spectral information to identify, or at least differentiate between, different materials in a scene. Some embodiments may capture lower spectral resolution than others, and thus have less accuracy in identifying materials. Nevertheless, even low spectral resolution information may allow for differentiation between different materials that would have better performance than material discrimination using conventional red, green and blue imaging systems.

Figure 2:
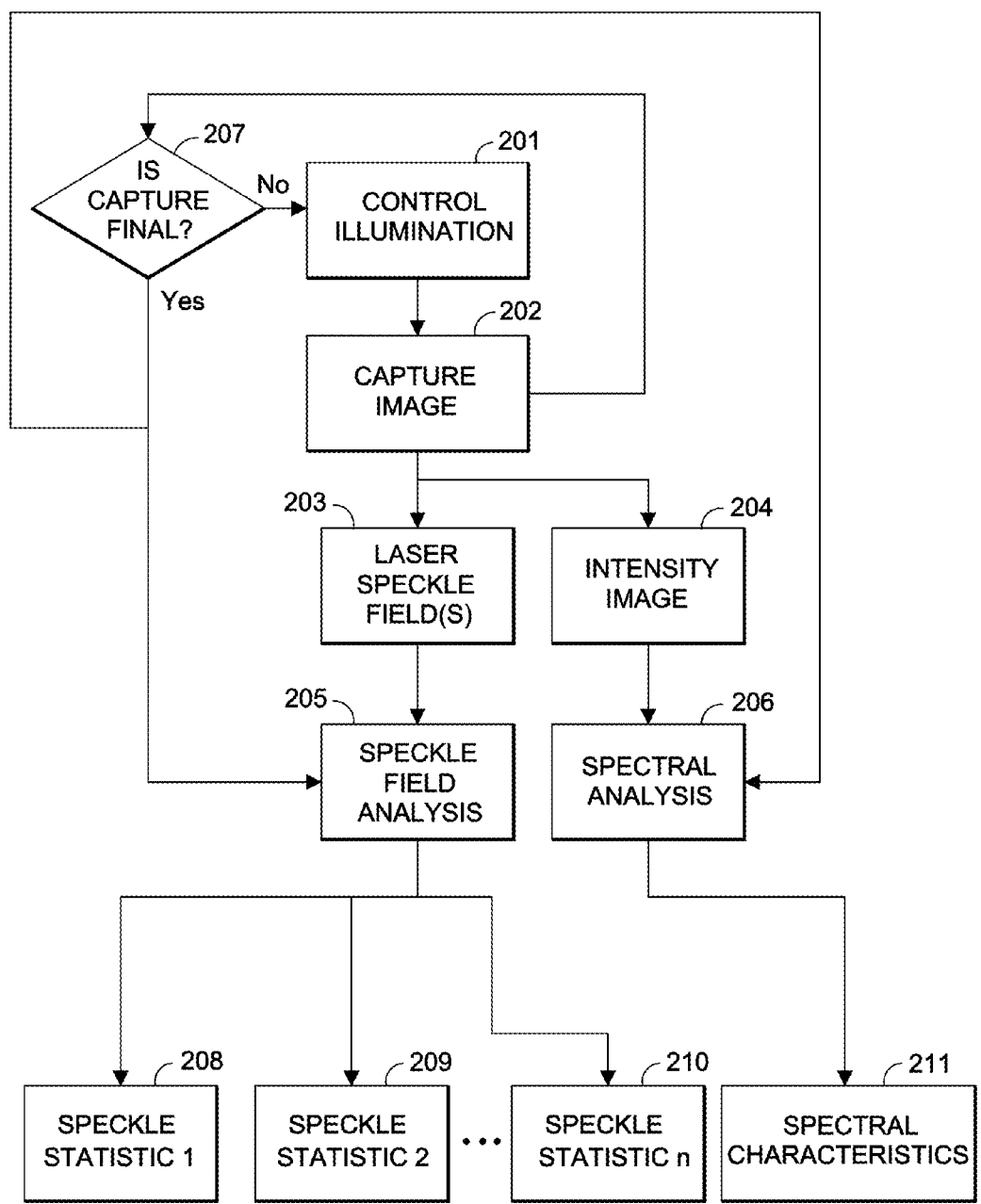
FIG. 2 is a block diagram for explaining a material identification apparatus according to an example embodiment.

FIG. 2 is a block diagram for explaining processing in a material identification apparatus, such as identification device 100. Generally, the identification device includes at least one illumination source of controlled coherence properties (e.g., light source 101A and/or 101B) that produces a speckle pattern. If there is more than one light source, the light sources can be used simultaneously or sequentially. In addition, one or more images of the illuminated material are acquired by one or more sensors, such as sensors 102A and 102B. The captured images are analyzed by calculating the spectral response of the material to one or more illuminations. The speckle field image, meanwhile, is analyzed to provide statistical values.

As shown in FIG. 2, in block 201, illumination is controlled so as to illuminate a material (e.g., material 103) with a light of controlled coherence properties. The light source which emits the light of controlled coherence properties may include a laser light source such as light source 101A. Moreover, the material may be illuminated at multiple different illumination angles or wavelengths by, for example, using multiple light sources such as light source 101A and light source 101B.

In block 202, one or more images are captured, for example by sensors 102A and/or 102B. In particular, image data of the light reflected from the illuminated material may be captured by spectral sensors 102B, and the image data may be analyzed for spectral characteristics. Image sensor 102A also senses one or more speckle patterns which result from interference of reflected light waves when material 103 is illuminated with light from light source(s) 101A and/or 101B having controlled coherence properties. Thus, as shown in FIG. 2, image capture in block 202 results in laser speckle field(s) 203 and a (spectral) intensity image 204.

In blocks 205 and 206, there is analysis of speckle field statistics and spectral characteristics, respectively. For example, speckle field analysis may comprise derivation of speckle contrast or monochromatic contrast over the captured speckle field, or cross-correlation of multiple speckle fields, as described more fully below.

Thus, as a result, speckle statistics such as speckle statistics 1, 2 . . . n (shown by blocks 208, 209 and 210) are obtained, along with spectral characteristics 211. The spectral characteristics and speckle statistics are compared against plural entries in a database. Each entry in the database correlates the identity of a material against a corresponding spectral characteristic and a corresponding speckle statistic for the material.

In one embodiment, the spectral characteristics and/or speckle statistics can be collected into a feature vector, and material discrimination is performed by comparing the feature vectors of materials. In that regard, machine learning could be performed for material identification using a set of training feature vectors, in order to identify unknown materials.

FIG. 3A is a simplified block diagram for explaining discrimination between a material A and a material B from the captured statistics and characteristics according to an example embodiment. For material A, speckle statistics 1, 2, . . . n (shown as speckle statistics 301, 302 and 303) and spectral characteristics 304 are input to material identification module 300. In addition, material B speckle statistics 1, 2, . . . n (shown as speckle statistics 305, 306 and 307) and spectral characteristics 308 are input to material identification module 300. An assessment of material discrimination 309 is output which is the determination whether material A and material B are the same material or not. In another embodiment, the assessment of material discrimination includes a probability that material A and material B are the same material.

FIG. 3B is a view for explaining a material identification module according to one example embodiment. Identification module 300 comprises computer-executable process steps stored on a non-transitory computer-readable storage medium, such as memory 107. More or less modules may be used, and other architectures are possible.

As shown in FIG. 3B, identification module 300 includes at least an illumination module 351 for illuminating the material with one or more light sources including at least one light source which emits light of controlled coherence properties. To that end, illumination module 351 may, for example, be executed by processor 106 in order to drive illumination system 104 and light source(s) 101A and/or 101B and to drive capture system 105 and sensor(s) 102A and/or 102B. A deriving module 352 is for deriving both of a spectral characteristic and a speckle statistic. The spectral characteristic and speckle statistic are derived from the captured image of light reflected from the illuminated material. The material identification module 300 further includes a comparison module 353 for comparing the spectral characteristic and speckle statistic against plural entries in a database. To that end, comparison module accesses a database which, in the example shown in FIG. 3B, is stored in memory 107. Each entry in the database correlates the identity of a material against a corresponding spectral characteristic and a corresponding speckle statistic for the material. Additionally, the material identification module 300 includes a determination module 354 for determining at least one candidate for the identity of the illuminated material based at least in part on the comparison. In another embodiment, determination module 354 determines a probability distribution function of the identity of the illuminated material based at least in part on the comparison, wherein each candidate material identity is associated with a probability.

Figure 4:
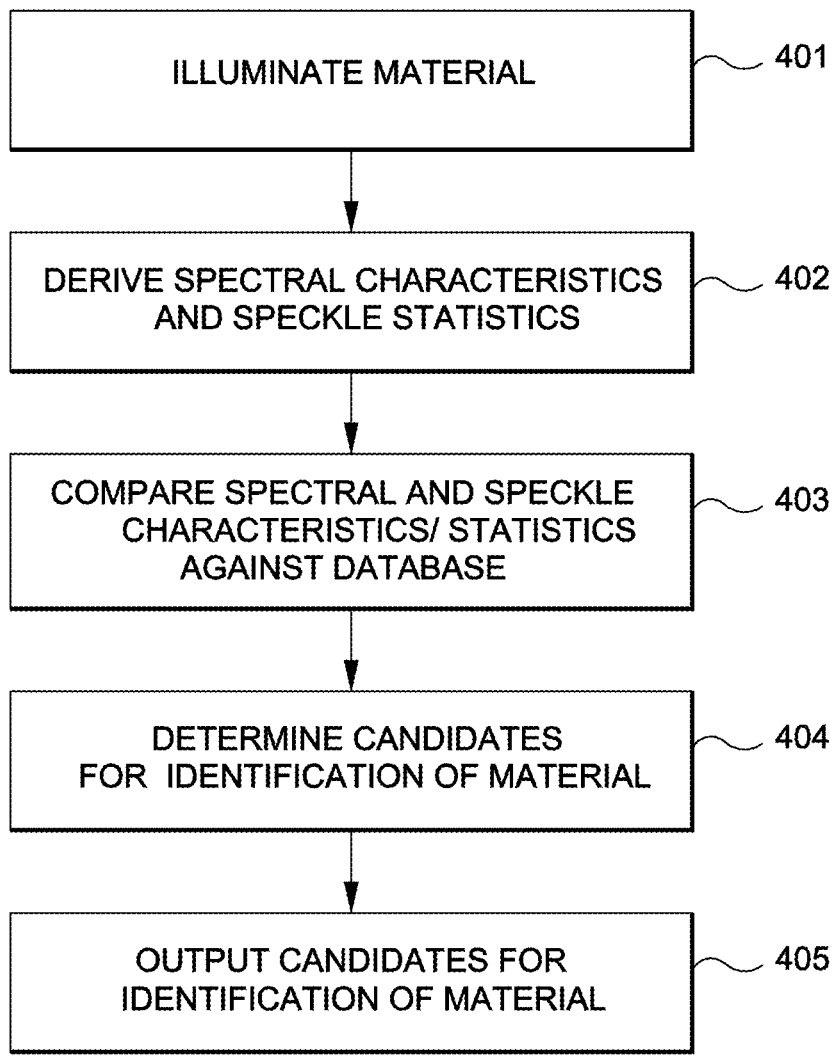
FIG. 4 is a flowchart for explaining processing in the identification device shown in FIGS. 1A and 1B according to an example embodiment.

FIG. 4 is a flowchart for explaining processing in the identification device shown in FIGS. 1A and 1B according to an example embodiment.

Briefly, as shown in FIG. 4, a material is illuminated with one or more light sources including at least one light source which emits light of controlled coherence properties. Both of a spectral characteristic and a speckle statistic are derived using light reflected from the illuminated material. The spectral characteristic and the speckle statistic are compared against plural entries in a database. Each entry in the database correlates the identity of a material against a corresponding spectral characteristic and a corresponding speckle statistic for the material. At least one candidate for the identity of the illuminated material is determined based at least in part on the comparison.

Turning to FIG. 4, in step 401, the material is illuminated with one or more light sources including at least one light source which emits light of controlled coherence properties.

In step 402, both of spectral characteristics and speckle statistics are derived using light reflected from the illuminated material.

Several approaches are possible for speckle analysis. Ordinarily, deriving the speckle statistic includes capture of a speckle field reflected from the illuminated material, and analysis of the captured speckle field. Although surface roughness is generally a derivative of the analysis of the captured speckle filed, the disclosure is not limited to this material property. Surface roughness generally refers to the variation of heights of the surface profile of the material. Surface heights can be modeled as a random variable h. One measure to characterize surface roughness is the root mean square (RMS) surface roughness $\sigma_h$, i.e., the standard deviation of the surface height h. Other measures of surface roughness may be used, such as $R_a$, the average of absolute values:

$$R_a = \langle |h - \langle h \rangle| \rangle$$

In this regard, in most situations, it may not be necessary to determine a measure of surface roughness to distinguish between materials, and rather the speckle statistics may be used directly as components of a feature vector of a material, which is then compared with other feature vectors. Thus, in some embodiments, surface roughness is not derived, and rather statistics from the speckle field are derived.

In one example, the speckle statistic includes a speckle contrast, and analysis of the captured speckle field comprises derivation of speckle contrast over the captured speckle field. In another example, the light source which emits light of controlled coherence properties includes a monochromatic light source, the speckle statistic includes a monochromatic contrast, and analysis of the captured speckle field comprises derivation of monochromatic contrast over the captured speckle field.

In still another example, the one or more light sources include multiple coherent light sources including first and second laser light sources with respectively different wavelengths (applied simultaneously or sequentially), respective first and second speckle fields are captured, the speckle statistic comprises a wavelength correlation, and analysis of the captured first and second speckle fields includes cross-correlation of the captured first and second speckle fields.

In yet another example, the light source which emits light of controlled coherence properties includes one or more laser light sources, the material is coherently illuminated at multiple different illumination angles including at least first and second illumination angles, and respective first and second speckle fields are captured. The speckle statistic includes an angle correlation, and analysis of the captured first and second speckle fields includes cross-correlation of the captured first and second speckle fields.

In an even further example, the light source which emits light of controlled coherence properties includes a polychromatic light source with finite coherence length, the speckle statistic includes a polychromatic speckle contrast, and analysis of the captured speckle field comprises derivation of polychromatic speckle contrast over the captured speckle field.

In one embodiment, the speckle statistic comprises a gray level co-occurrence matrix (GLCM), and analysis of the captured speckle field comprises derivation of the GLCM over the captured speckle field, and texture analysis to extract textural features. In another embodiment, the speckle statistic comprises a digital counts per second (DCPS), and analysis of the captured speckle field comprises derivation of DCPS over the captured speckle field. In other embodiments, the speckle statistic includes a skewness defined by the standard 3rd statistical moment, and analysis of the captured speckle field includes derivation of skewness over the captured speckle field. In still other embodiments, the speckle statistic includes a kurtosis defined by the standard 4th statistical moment, and analysis of the captured speckle field includes derivation of kurtosis over the captured speckle field. In still another embodiment, the spectral characteristic includes spectral reflectance, and plural speckle statistics are derived including at least a speckle contrast and a speckle patch size.

Meanwhile, deriving the spectral characteristic includes spectral analysis of the light reflected from the illuminated material. For example, the light source which emits light of controlled coherence properties includes a laser light source, and spectral analysis includes capture of light reflected from the illuminated material with a spectral sensor. In another example, the one or more light sources include multiple coherent light sources, each comprised of a laser with a respectively different wavelength, and spectral analysis includes capture of light reflected from the illuminated material with a spectral sensor. In still another example, the one or more light sources include at least one incoherent light in conjunction with a laser light source, and spectral analysis includes capture of light reflected from the illuminated material with a spectral sensor.

In step 403, the spectral characteristics and speckle statistics are compared against plural entries in a database stored in, for example, memory 107. Each entry in the database correlates the identity of a material against a corresponding spectral characteristic and a corresponding speckle statistic.

In step 404, at least one candidate for the identity of the illuminated material is determined based at least in part on the comparison. In one embodiment, to determine a candidate or candidates, a probability distribution function of the identity of the illuminated material is determined based at least in part on the comparison, and each candidate material identity is associated with a probability. The candidate or candidates are then determined in accordance with those materials having high likelihood of being the illuminated material, as indicated by the probability function.

In step 405, the candidate(s) for the identity of the illuminated material are output via, for example, output system 109.

A number of approaches for obtaining speckle statistics will now be described. It should be understood that these approaches are merely examples, and numerous other approaches are possible.

One statistic which can be derived from a speckle field is speckle contrast. Speckle contrast is defined as $C = \sigma_I/\mu_I$ where $\mu_I$ is the average of I, $\sigma_I$ is the standard deviation of I, and I is the intensity of the speckle field.

Monochromatic speckle contrast refers to the speckle contrast of a speckle field resulting from a monochromatic coherent light source. If it is necessary to derive surface roughness, a basic technique deduces surface roughness and surface-height correlation area from monochromatic speckle contrast when the scattering surface is relatively smooth.

It can be shown that the monochromatic speckle contrast C can be expressed as a function of $N_0$ and normalized RMS surface roughness $\sigma_h/\lambda$, where $N_0$ is the number of surface height correlation areas lying within the equivalent area of the PSF (point spread function) of the imaging system:

$$C = \left\{ \frac{8(N-1)\left[N - 1 + \cosh\left(\left(4\pi\frac{\sigma_h}{\lambda}\right)^2\right)\right]\sinh^2\left(\frac{1}{2}\left(4\pi\frac{\sigma_h}{\lambda}\right)^2\right)}{N\left(N - 1 + \exp\left(\left(4\pi\frac{\sigma_h}{\lambda}\right)^2\right)\right)} \right\}^{\frac{1}{2}} \quad (1a)$$

$$N = \frac{N_0(\exp(\sigma_\phi^2) - 1)}{Ei(\sigma_\phi^2) - \varepsilon - \ln(\sigma_\phi^2)} \quad (1b)$$

$$\sigma_\phi = \left(\frac{4\pi}{\lambda}\right)\sigma_h \quad (1c)$$

In the above equations, Ei is the exponential integral function, $\varepsilon$ is the Euler constant, $\lambda$ is the wavelength of the light, and $\sigma_h$ is the standard deviation. For known $N_0$, a measurement of speckle contrast yields a unique value for the normalized RMS roughness $\sigma_h/\lambda$, provided that $\sigma_h \ll \lambda$. When the RMS roughness becomes comparable with the laser wavelength, the curves saturate at the value 1, and it is no longer possible to deduce the roughness from the speckle contrast. Thus, in practice, the laser wavelength may impose a natural upper limit of measurable roughness using this method of monochromatic speckle contrast.

In another approach, wavelength correlation can be performed. In this method, two lasers with different wavelengths are used. The normalized cross-correlation $\mu_A$ is a speckle statistic. If it is necessary to derive surface roughness, it can be shown that (assuming that the surface roughness obeys Gaussian statistics) the normalized cross-correlation $\mu_A$ of the two speckle fields at wavelengths $\lambda_1$ and $\lambda_2$ is given by:

$$|\mu_A|^2 = \exp\left[-\left(2\pi\frac{\sigma_h}{\bar{\lambda}}\frac{|\Delta\lambda|}{\bar{\lambda}}\right)^2\right] \quad (2a)$$

$$\bar{\lambda} = \frac{\lambda_1 + \lambda_2}{2} \quad (2b)$$

The correlation operation can be performed using a double exposure technique, for example. Thus, the measurement system would detect one speckle field with laser wavelength $\lambda_1$ and a second with wavelength $\lambda_2$, and the two speckle fields would be correlated. If it is further necessary to derive the surface roughness, it is possible to determine the value of $\sigma_h/\bar{\lambda}$ from $\mu_A$ and $\Delta\lambda$. from equations (2a) and (2b). In this way, the surface roughness can be obtained. The applicable RMS roughness range for this method is generally from about 0.1 micron to 1 micron.

Still another approach which can be used is angle correlation. Similar to the wavelength correlation method, angle correlation $\lambda_A$ is a speckle statistic. It is possible to obtain surface roughness information with two different angles of illumination using a monochromatic laser. It can be shown that the normalized cross-correlation of the two resulting speckle fields is given by $$|\mu_A|^2 = \exp\left[-\left(2\pi\frac{\sigma_h}{\bar{\lambda}}\Delta\theta_i\sin\theta_i\right)^2\right], \quad (3)$$

where $\theta_i$ is the initial angle of illumination, and $\Delta\theta_i$ is the change in angle of illumination. The shift of the second speckle field required is $\Delta\theta_i z$ in the direction opposite to the direction of the illumination shift, where z is the distance from the sample surface to the sensor plane. Thus, given a measured correlation between the properly shifted speckle fields, and knowing the change in angle that was made between measurements, the normalized RMS roughness can be obtained.

Yet another approach is polychromatic speckle contrast. In that regard, one way to extend the usable RMS roughness range is to increase the path difference of the elementary scattered waves, up to the order of the coherence length of the light source. One implementation of this idea is through the use of polychromatic light source with finite coherence length. The speckle contrast of the resulting speckle field is referred to as polychromatic speckle contrast.

Figure 5:
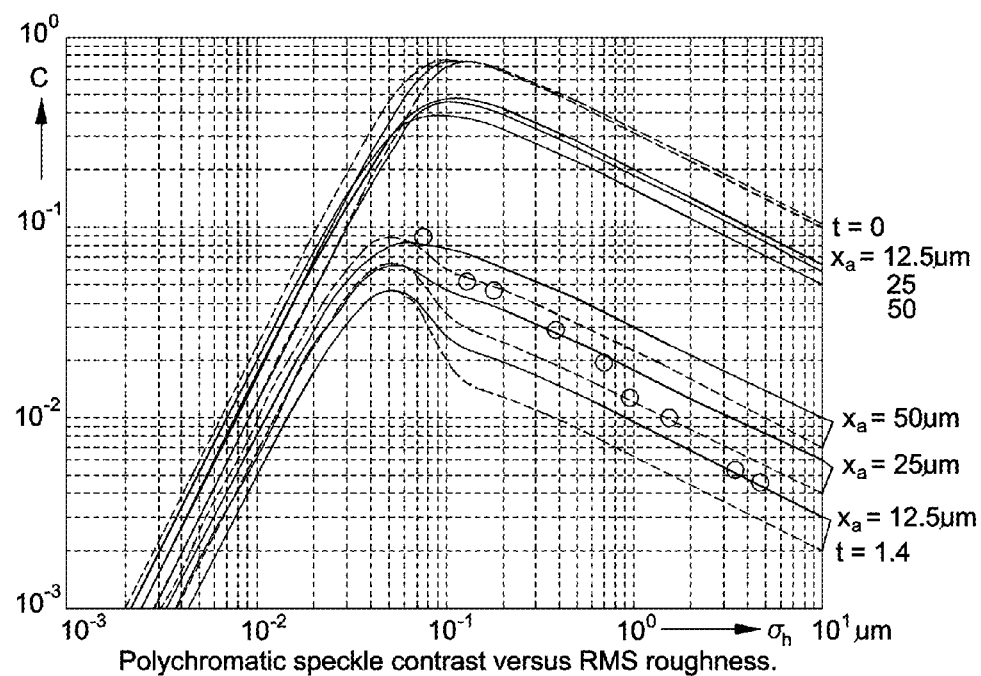
FIG. 5 is a view for explaining an analytical relationship between speckle contrast and RMS roughness for light sources with various levels of incoherence.

FIG. 5 shows a plot of an analytical relationship between polychromatic speckle contrast and RMS roughness for light sources with various levels of incoherence, as described in Leonhardt, et al., "Removing ambiguities in surface roughness measurement", Optica Acta, vol. 29, no. 4, 493-499, 1982. t is a parameter that measures incoherence, with t=0 indicating that the light source is coherent. It can be seen that the monotone decreasing piece of the graph has a larger span as incoherence is introduced into the light source. With polychromatic speckle contrast, the measurable RMS roughness range is from 0.5 micron to 5 microns.

Another statistical approach is the gray level co-occurrence matrix (GLCM). If necessary, surface roughness information can be extracted by texture analysis of the speckle pattern via GLCM.

Figure 6:
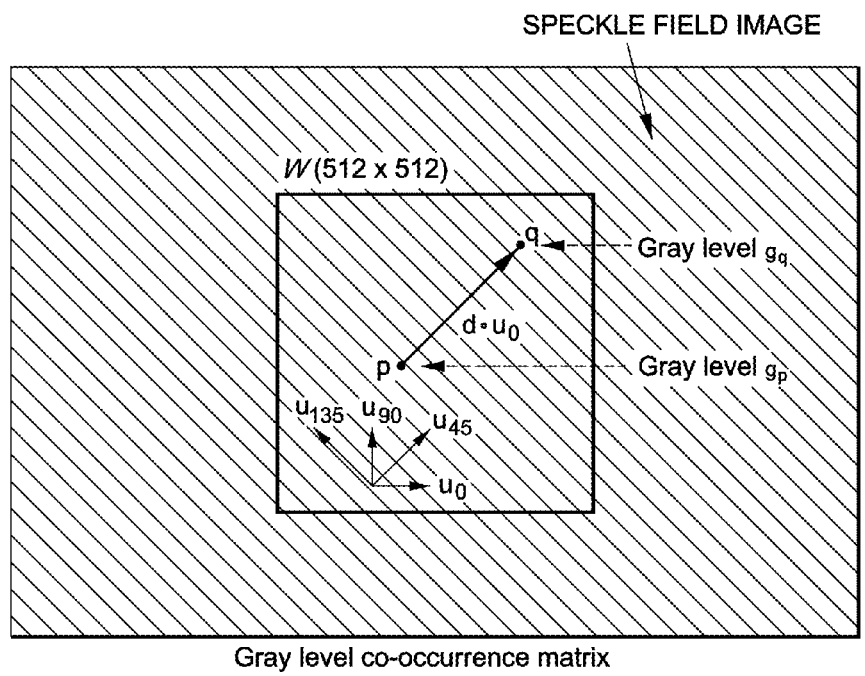
FIG. 6 is a view for explaining a gray level co-occurrence matrix (GLCM) according to an example embodiment.

In that regard, to derive the GLCM, a window W of the speckle field image is chosen, for example, of size 512×512 as shown in FIG. 6.

Next, the digital values in the speckle field are binned into n levels, say n=256. For each of the four directions θ=0,45.90, 135, and pixel offset distance d=1,2,3, . . . , define $$M(d,\theta) = (P_{ij})_{i,j=0,1,\ldots,n-1} \quad (4a)$$

$$P_{ij}(d,\theta) = \#\{\{p,q\} | p,q \in W, g_p=i, g_q=j, p-q=\alpha u_\theta, |\alpha|=d\} \quad (4b)$$

$$\hat{P}_{ij}(d,\theta) = P_{ij}(d,\theta)/\Sigma_{i,j=0}^{n-1} P_{ij}(d,\theta) \quad (4c)$$

From the GLCM $\hat{P}_{ij}(d,\theta)$, 14 textural features have been proposed in M. Haralick et al., "Texture features for image classification", IEEE Trans. Syst. Man. Cybern., vol. 3, 610-621, 1973. Four of them, namely "contrast", "correlation", "energy", "homogeneity", may be selected. For example, the GLCM energy is defined as follows:

$$e_\theta(d) = \sum_{i,j=0}^{n-1} \left(\hat{P}_{ij}(d,\theta)\right)^2 \quad (5)$$

For each textural feature, a feature curve for each of the four directions (0°, 45°, 90°, 135°) is determined as a function of pixel offset distance d, and an exponential curve is fitted using all four feature curves:

$$y = y_0 + k \exp(-d/\sqrt{\sigma}), \quad (6)$$

where $y_0$, k, and σ are the parameters to be determined, d is the pixel offset distance and y is the textural feature value. In addition, to reduce the influence of the variances of amplitudes and offsets, each of the four feature curves is normalized beforehand by taking the Z-score.

Figure 7:
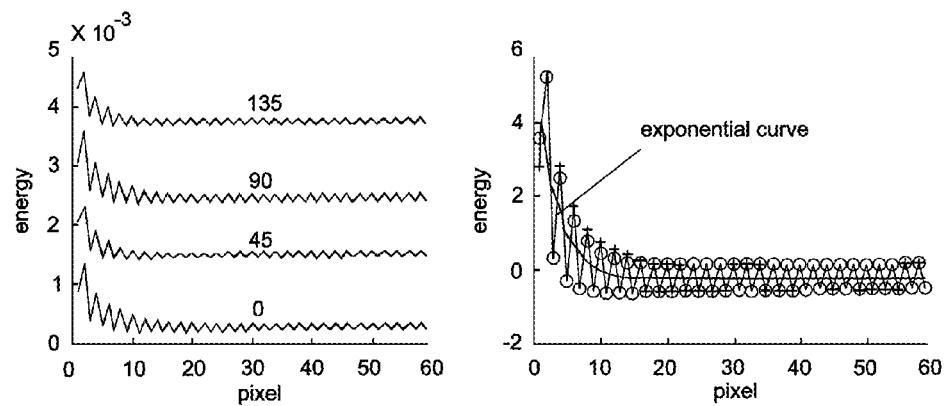
FIG. 7 is a view for explaining a fitting process for an energy feature.
Figure 8:
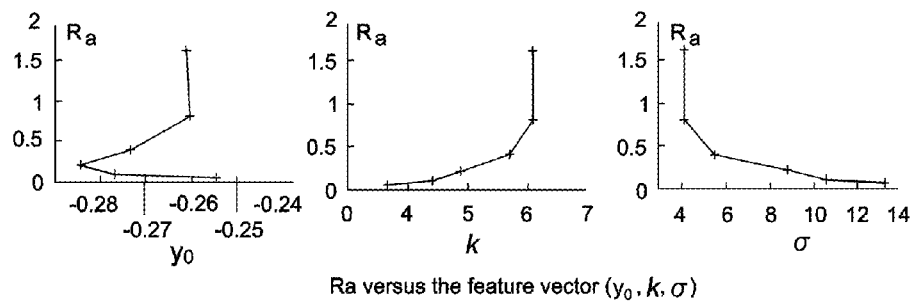
FIG. 8 is a view for explaining a relationship between surface roughness $R_a$ and energy feature fitting parameters.

FIG. 7 illustrates the fitting process for the energy feature. Meanwhile, FIG. 8 illustrates the relationship between surface roughness $R_a$ and the energy feature fitting parameters.

The energy curve for each direction is normalized by taking the standard Z-score:

$$E_\theta = Z[e_\theta] = \frac{e_\theta - \mu[e_\theta]}{\sigma[e_\theta]} \quad (14)$$

Finally, all 4 curves are fitted to exponential function with parameters k, A, λ:

$$E = k + A \exp(-\lambda d) \quad (15)$$

Figure 9:
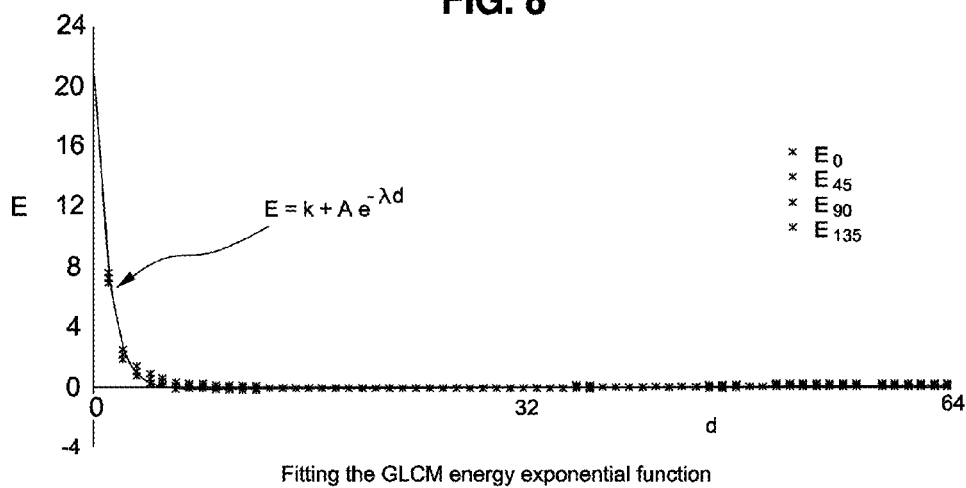
FIG. 9 illustrates another example of a fitting process for the energy feature.

FIG. 9 shows an example of this fitting with actual speckle data. The energy feature fitting parameters, which are themselves statistics derived from the speckle field, may form a feature vector for material discrimination and identification. It is also possible to extract surface roughness through the relationship between the feature vector and surface roughness, as depicted in FIG. 8.

Other statistics can be used. Other example approaches and statistics include, for example, Digital Count Per Second (DCPS), skewness, and kurtosis. Moreover, while many of the above statistics described can be used to estimate surface roughness, it should be understood that these statistics can be used directly as all or part of a feature vector. For example, in some cases, it might be more efficient to simply compare the speckle contrasts of two materials.

With regard, to DCPS, if exposure time is 1/v seconds, then DCPS=$\mu_W \cdot v$. This normalization allows for comparison of speckle fields captured with different exposure time. Varying exposure time in capture can be helpful because different materials have different spectral reflectance. For example, dark material may require more exposure time so that the captured speckle intensity is significantly above the sensor noise level.

Skewness, meanwhile, is the standard $3^{rd}$ statistical moment. Skewness is a measure of the asymmetry of the probability distribution of a real-valued random variable, and in this context is defined as:

$$s = \frac{\langle(g-\mu_W)^3\rangle_W}{\sigma_W^3}. \quad (16)$$

Kurtosis is the standard $4^{th}$ statistical moment. Kurtosis is a measure of the "peakedness" of the probability distribution of a real-valued random variable, and in this context is defined as:

$$k = \frac{\langle(g-\mu_W)^4\rangle_W}{\sigma_W^4}. \quad (17)$$

Figure 15:
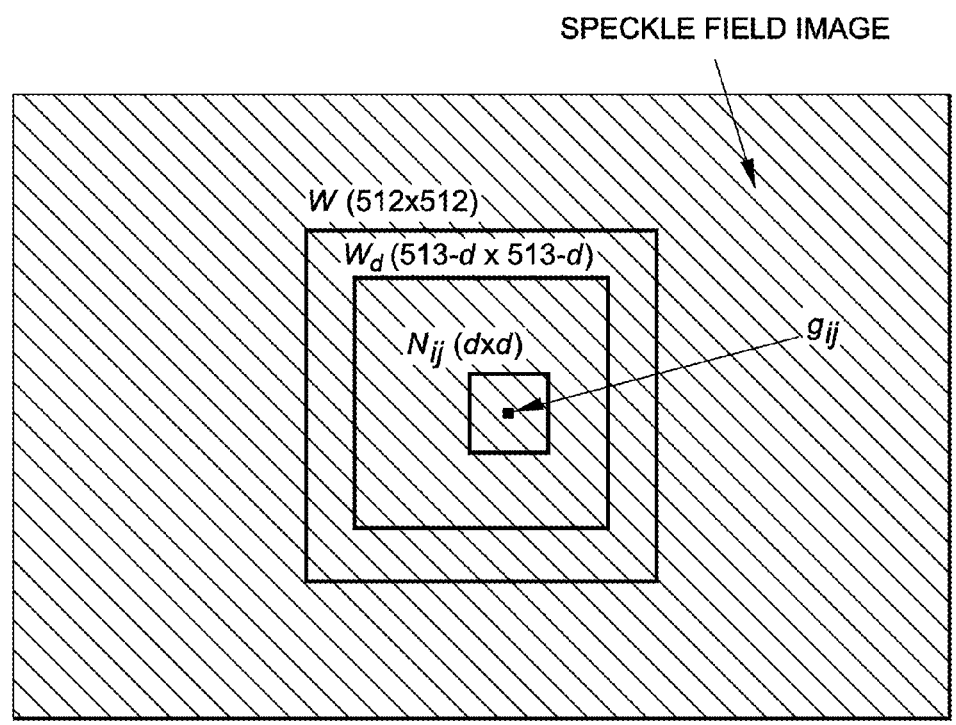
FIGS. 15 and 16 are views for explaining a speckle patch size according to example embodiments.

Yet another statistic that can be derived from a speckle field is the speckle patch size. Refer now to FIG. 15. Choose a window W, of size 512×512, for example. Denote by g the 512×512 intensity field. Then we can calculate the average speckle intensity within this window:

$$\mu_W = \langle g \rangle_W = \frac{\sum_{(i,j)\in W} g_{ij}}{(512)^2}$$

Similarly, we can calculate the standard deviation $\sigma_W$. As before, the speckle contrast within this window is defined as:

$$C = \frac{\sigma_W}{\mu_W}$$

A local version of speckle contrast can also be defined. First of all, the "local speckle contrast" at pixel location (i, j) is defined as:

$$C_{ij} = \sigma_{N_{ij}}/\mu_{N_{ij}}$$

where $N_{ij}$ is a d×d neighborhood centered at (i, j). Then we consider the average local speckle contrast:

$$c_d = \frac{\sum_{(i,j)\in W_d} C_{ij}}{(513-d)^2}$$

Note that the number of pixels that have local speckle contrast statistic is a function of d: As d gets larger, fewer pixels have a d×d neighborhoods that lie completely inside W. In the limit, when d=512, only 1 pixel has local speckle contrast, and $C_{512}$ coincides with the (global) speckle contrast C.

Next, we define the normalized average local speckle contrast:

$$\hat{c}_d = \frac{c_d}{c_{512}}$$

Figure 16:
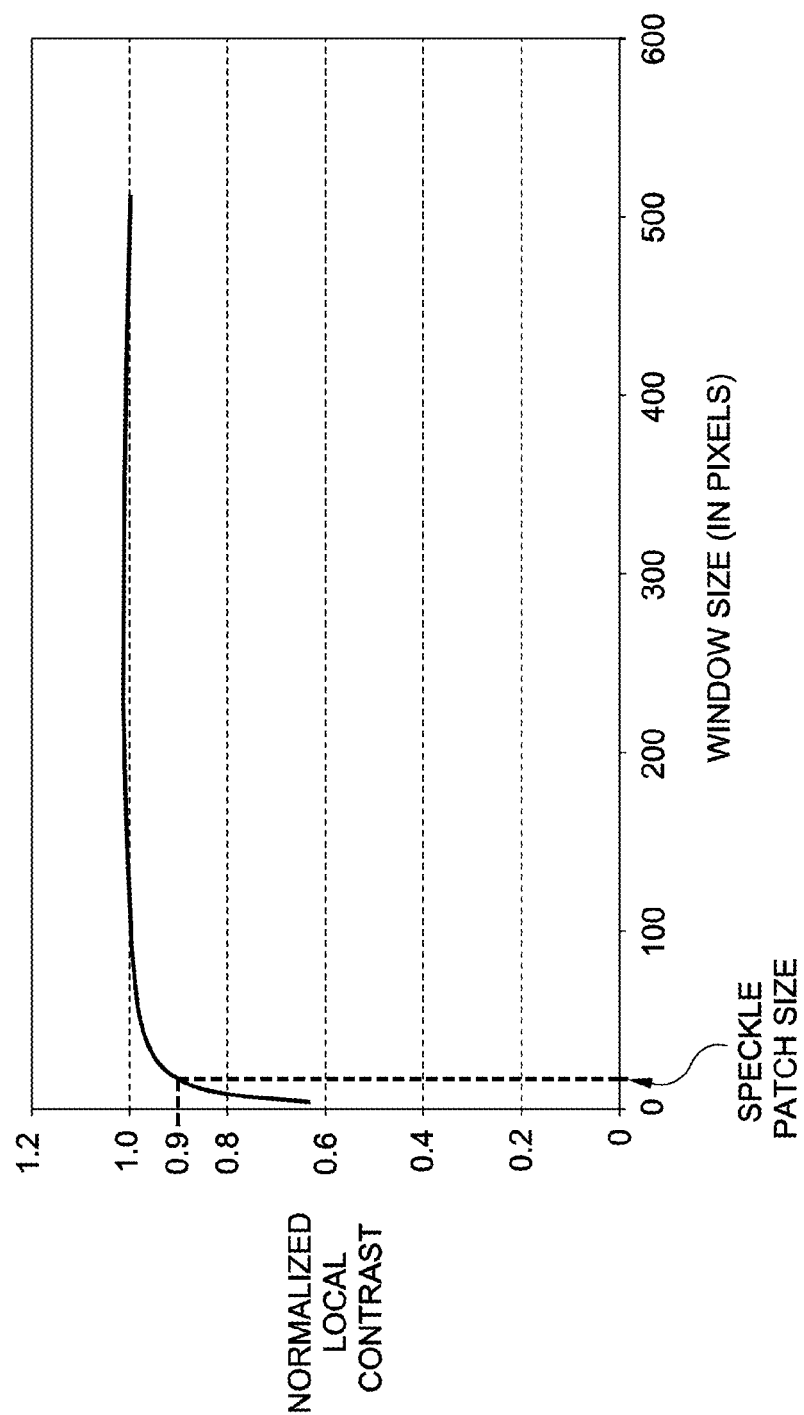

Intuitively, as d increases towards the maximum value 512, $\hat{c}_d$ tends to 1. FIG. 16 shows a plot of $\hat{c}_d$ against d using actual measured data. The rippling of $\hat{c}_d$ as it approaches 1 is likely a statistical effect.

To avoid the rippling and also numerical instability due to the near horizontal asymptote, we chose a value of 0.9 to determine the speckle patch size. In other words, the speckle patch size is the size of the window at which the normalized local contrast attains 90% of its maximum value (which is 1).

The speckle patch size is a 2nd order statistic, so it is immune to background DC noise, e.g., if a spatially constant stray intensity is added to the speckle field. In that sense, the speckle patch size is orthogonal to speckle contrast, which is a 1st order statistic.

Figure 10:
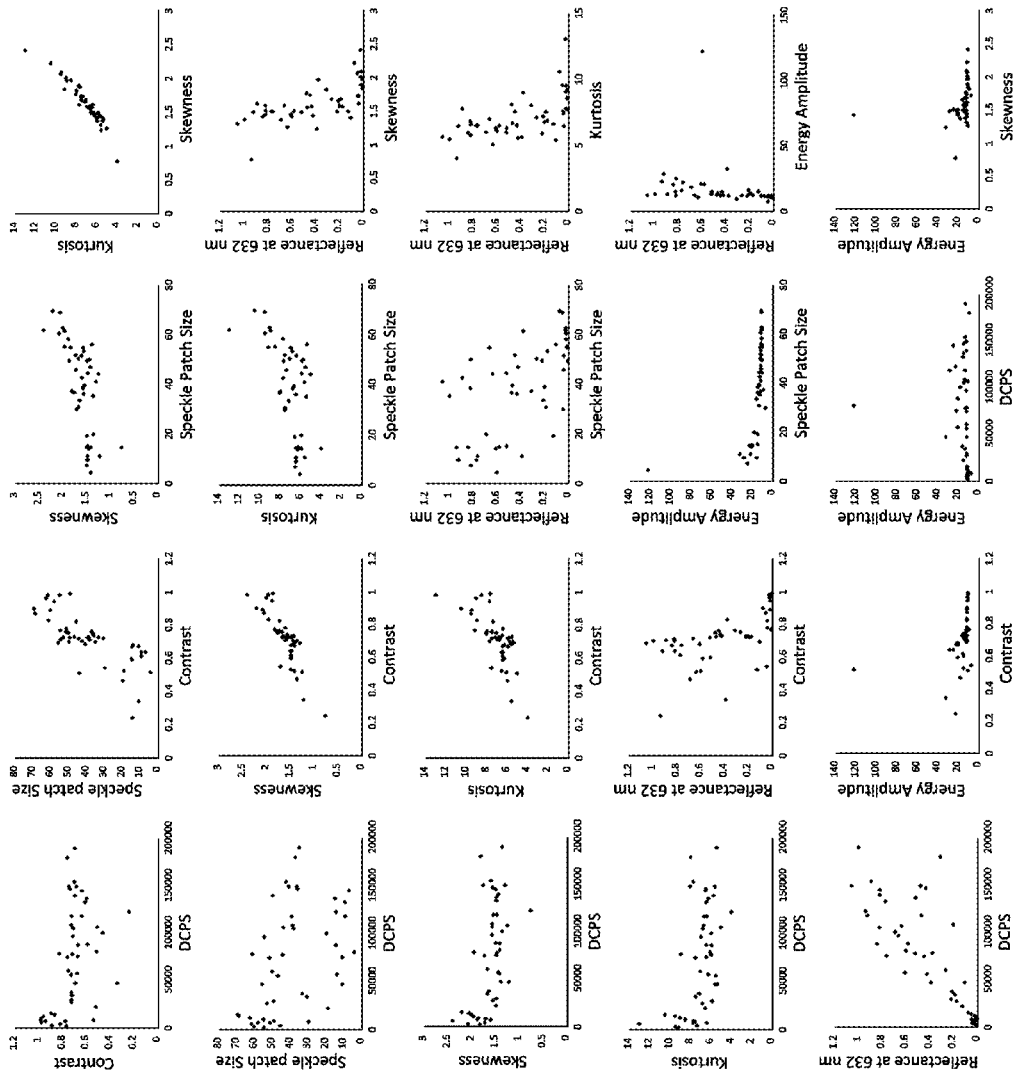
FIG. 10 is a view explaining plots of selected speckle statistics and/or spectral characteristics.

FIG. 10 is a view comparing different parameters of speckle statistics and spectral characteristics. In particular, FIG. 10 depicts a number of "versus plots" for measured samples, taken two features at a time. Generally, a small number of features should be chosen such that they are independent of each other. For example, it can be seen that skewness and kurtosis are highly correlated and should not be chosen together.

It should be understood that FIG. 10 is a visualization, and that in practice the relationship between all possible speckle and spectral variables may not be apparent from 2-dimensional versus plots.

Figure 12:
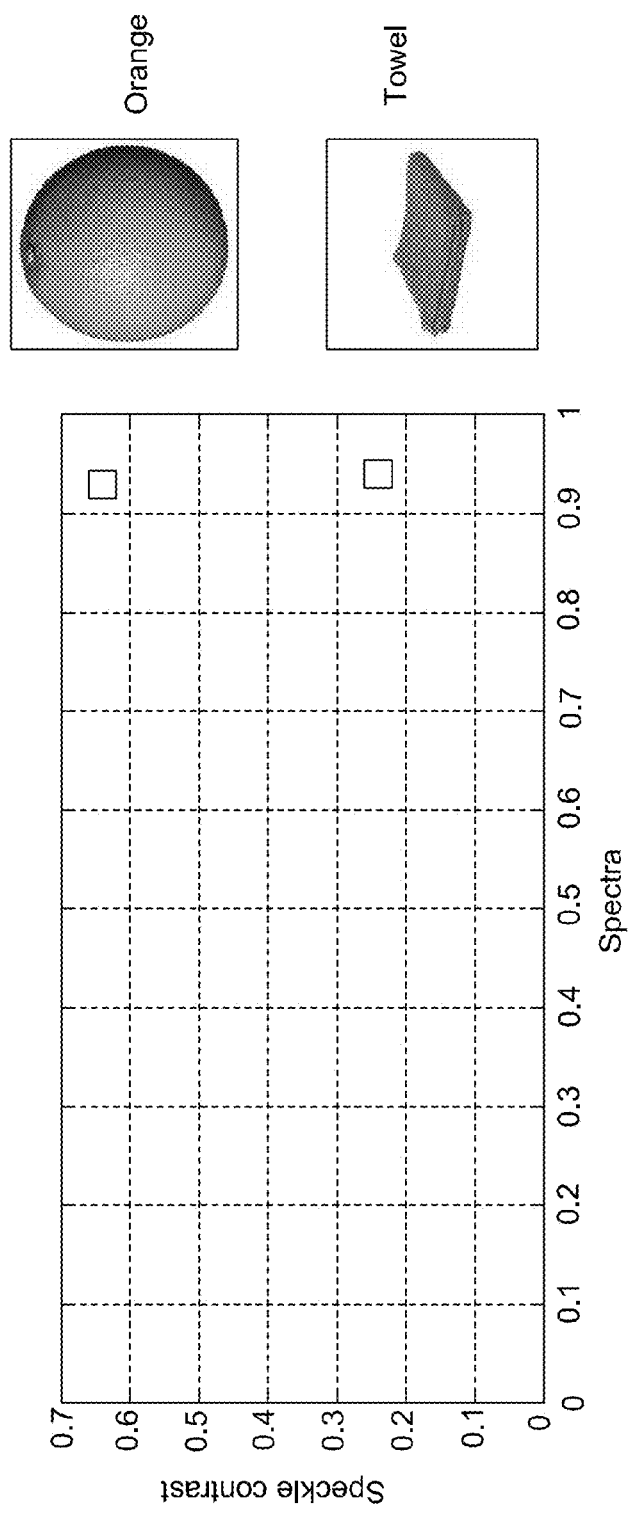
Figure 13:
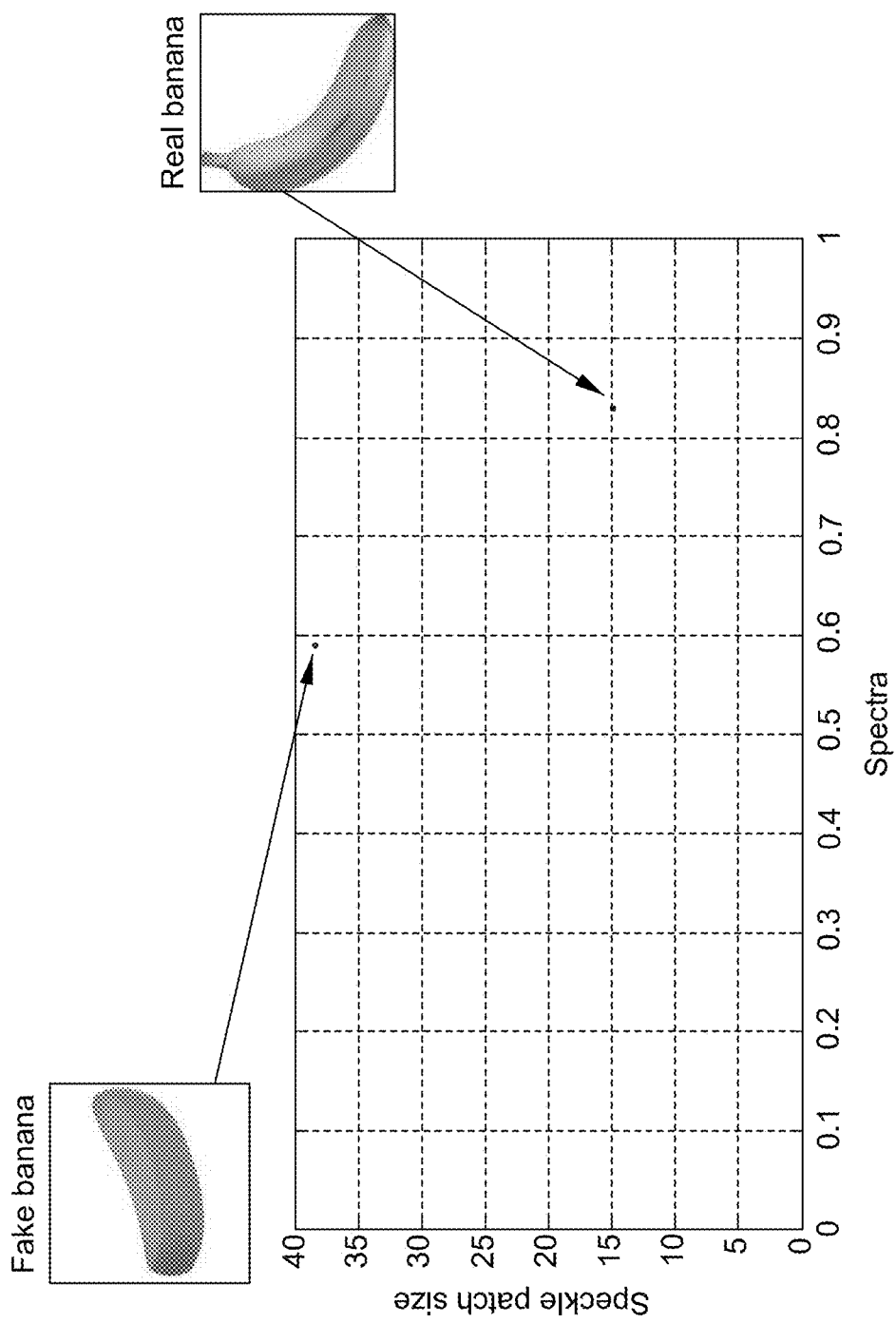

Based on the analysis shown in FIG. 10, it can be seen that it is ordinarily possible to combine the spectral and speckle information to discriminate between different materials. In one example using a spectral reflectance at 632 nm, and speckle contrast and speckle size as speckle statistics, different materials can be discriminated as shown in FIGS. 11 to 13.

Figure 11:
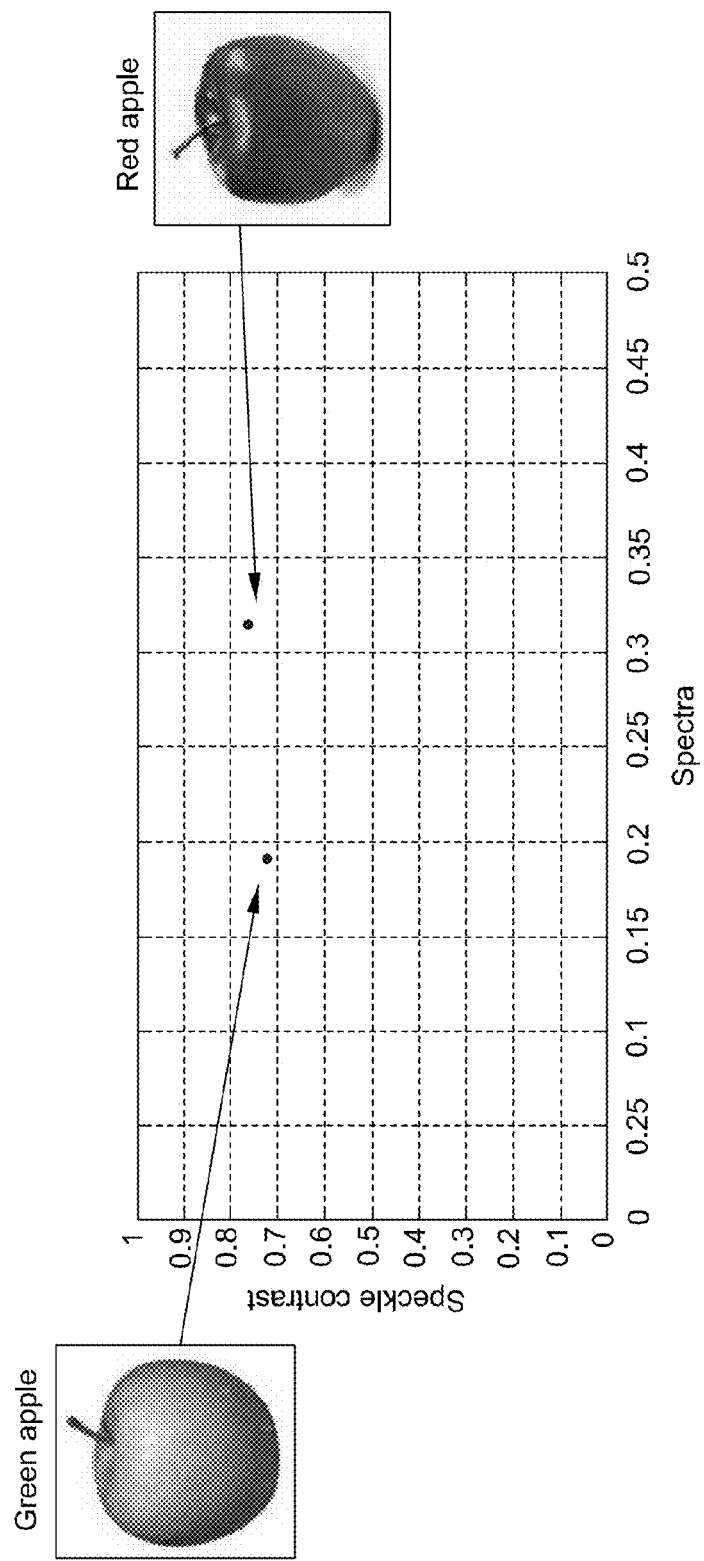
FIGS. 11 to 13 are views for explaining discriminating between different materials according to an example embodiment.

In particular, spectral information can be useful to discriminate materials with different colors, such as a green apple and a red apple shown in FIG. 11. In another example, speckle contrast could be used to discriminate materials with similar colors but different roughness, such as an orange and an orange towel as shown in FIG. 12. In still another example, speckle patch size could be useful to discriminate between natural and artificial materials such as a fake banana and a real banana, as shown in FIG. 13. Of course, these are simply examples, and many others are possible.

Figure 14:
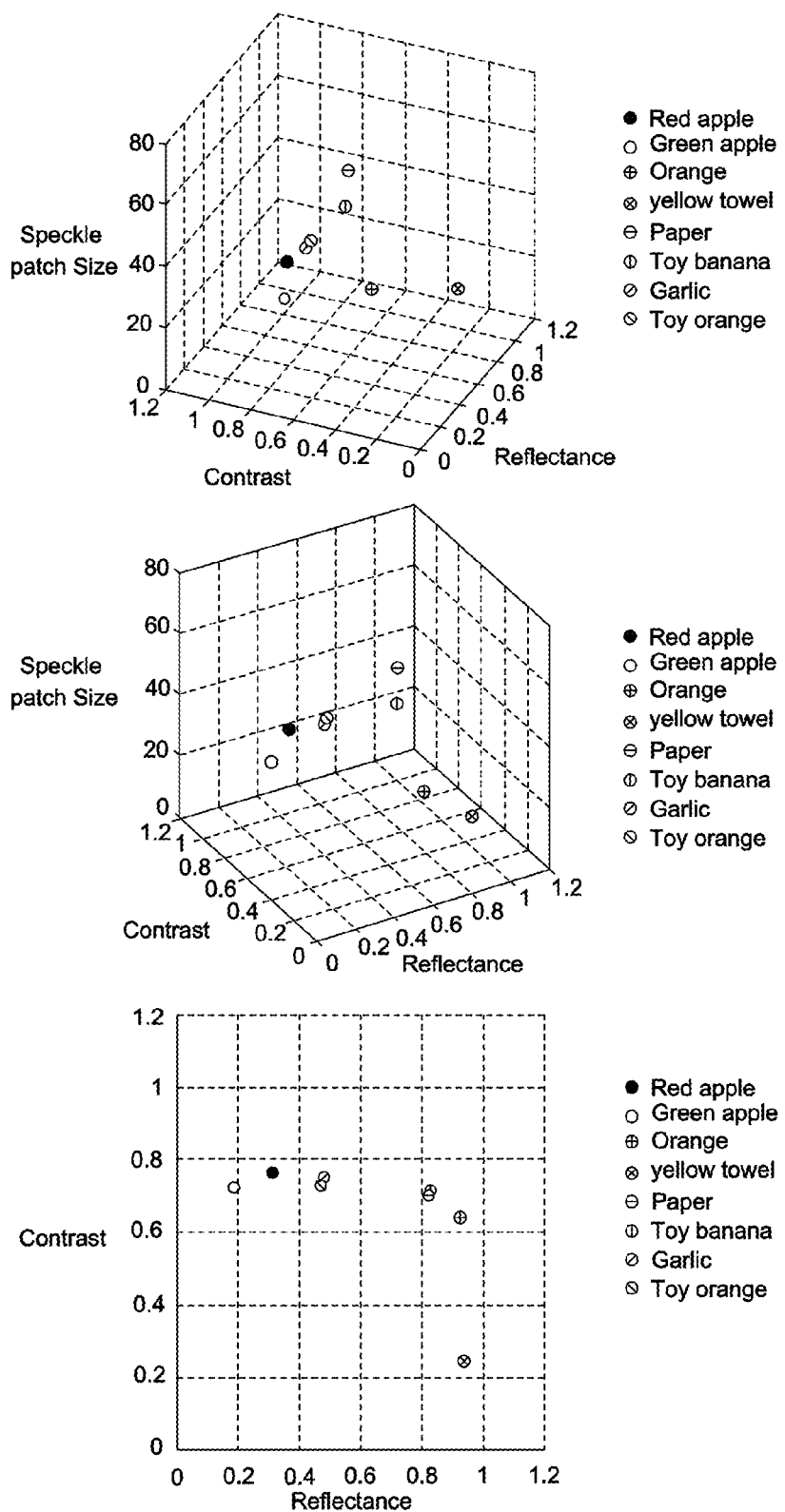
FIG. 14 is a view for explaining a feature space according to speckle and spectral information.

FIG. 14 is a view for explaining a feature space according to speckle and spectral information. In particular, FIG. 14 shows the feature space when the three example features used in FIGS. 11 to 13 (spectral reflectance, speckle patch size and speckle contrast) are all in play. In addition to the three sets of examples in FIGS. 11 to 13, there are plots of the features of garlic and a toy orange. In this specific case, these objects are not distinguishable based just on speckle patch size, and speckle contrast and reflectance features and other features need to be used to distinguish between these materials.

By comparing both spectral characteristics and speckle statistics against a database, it is ordinarily possible to perform a more robust discrimination between materials, including materials which might have similar surface roughness, similar spectral reflectance or other similarities.

<Other Embodiments>

According to other embodiments contemplated by the present disclosure, example embodiments may include a computer processor such as a single core or multi-core central processing unit (CPU) or micro-processing unit (MPU), which is constructed to realize the functionality described above. The computer processor might be incorporated in a stand-alone apparatus or in a multi-component apparatus, or might comprise multiple computer processors which are constructed to work together to realize such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. For these purposes, access to the non-transitory computer-readable storage medium may be a local access such as by access via a local memory bus structure, or may be a remote access such as by access via a wired or wireless network or Internet. The computer processor(s) may thereafter be operated to execute the computer-executable program or program steps to perform functions of the above-described embodiments.

According to still further embodiments contemplated by the present disclosure, example embodiments may include methods in which the functionality described above is performed by a computer processor such as a single core or multi-core central processing unit (CPU) or micro-processing unit (MPU). As explained above, the computer processor might be incorporated in a stand-alone apparatus or in a multi-component apparatus, or might comprise multiple computer processors which work together to perform such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. Access to the non-transitory computer-readable storage medium may form part of the method of the embodiment. For these purposes, access to the non-transitory computer-readable storage medium may be a local access such as by access via a local memory bus structure, or may be a remote access such as by access via a wired or wireless network or Internet. The computer processor(s) is/are thereafter operated to execute the computer-executable program or program steps to perform functions of the above-described embodiments.

The non-transitory computer-readable storage medium on which a computer-executable program or program steps are stored may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), micro-drive, a read only memory (ROM), random access memory (RAM), erasable programmable read only memory (EPROM), electrically erasable programmable read only memory (EEPROM), dynamic random access memory (DRAM), video RAM (VRAM), a magnetic tape or card, optical card, nanosystem, molecular memory integrated circuit, redundant array of independent disks (RAID), a nonvolatile memory card, a flash memory device, a storage of distributed computing systems and the like. The storage medium may be a removable function expansion unit inserted in and/or remotely accessed by the apparatus or system for use with the computer processor(s).

This disclosure has provided a detailed description with respect to particular representative embodiments. It is understood that the scope of the appended claims is not limited to the above-described embodiments and that various changes and modifications may be made without departing from the scope of the claims.

What is claimed is:

1. A method for identification of a material, the method comprising:
    illuminating the material with one or more light sources including at least one light source which emits light of controlled coherence properties;
    deriving both of a spectral characteristic and a speckle statistic, wherein the spectral characteristic and the speckle statistic are derived using light reflected from the illuminated material, wherein deriving the speckle statistic comprises capture of a speckle field reflected from the illuminated material, and analysis of the captured speckle field;
    comparing the spectral characteristic and the speckle statistic against plural entries in a database, wherein each entry in the database correlates the identity of a material against a corresponding spectral characteristic and a corresponding speckle statistic for the material; and
    determining at least one candidate for the identity of the illuminated material based at least in part on the comparison;
    wherein the one or more light sources include multiple coherent light sources including first and second laser light sources with respectively different wavelengths,
    wherein respective first and second speckle fields are captured,
    wherein the speckle statistic comprises a wavelength correlation, and
    wherein analysis of the captured first and second speckle fields comprises cross-correlation of the captured first and second speckle fields.

2. The method according to claim 1, wherein deriving the spectral characteristic comprises spectral analysis of the light reflected from the illuminated material.

3. The method according to claim 2, wherein the light source which emits light of controlled coherence properties comprises a laser light source, and wherein spectral analysis includes capture of light reflected from the illuminated material with a spectral sensor.

4. The method according to claim 2, wherein the one or more light sources include multiple coherent light sources, each comprised of a laser with a respectively different wavelength, and wherein spectral analysis includes capture of light reflected from the illuminated material with a spectral sensor.

5. The method according to claim 2, wherein the one or more light sources include at least one incoherent light in conjunction with a laser light source, and wherein spectral analysis includes capture of light reflected from the illuminated material with a spectral sensor.

6. The method according to any one of claim 4 or 5, wherein the light sources are applied simultaneously.

7. The method according to any one of claim 4 or 5, wherein the light sources are applied sequentially.

8. The method according to claim 1, wherein the first and second laser light sources are applied simultaneously.

9. The method according to claim 1, wherein the first and second laser light sources are applied sequentially.

10. A method for identification of a material, the method comprising:
   illuminating the material with one or more light sources including at least one light source which emits light of controlled coherence properties;
   deriving both of a spectral characteristic and a speckle statistic, wherein the spectral characteristic and the speckle statistic are derived using light reflected from the illuminated material, wherein deriving the speckle statistic comprises capture of a speckle field reflected from the illuminated material, and analysis of the captured speckle field;
   comparing the spectral characteristic and the speckle statistic against plural entries in a database, wherein each entry in the database correlates the identity of a material against a corresponding spectral characteristic and a corresponding speckle statistic for the material; and
   determining at least one candidate for the identity of the illuminated material based at least in part on the comparison;
   wherein the light source which emits light of controlled coherence properties comprises one or more laser light sources,
   wherein the material is coherently illuminated at multiple different illumination angles including at least first and second illumination angles,
   wherein respective first and second speckle fields are captured,
   wherein the speckle statistic comprises an angle correlation, and
   wherein analysis of the captured first and second speckle fields comprises cross-correlation of the captured first and second speckle fields.

11. The method according to claim 1, wherein the spectral characteristic includes spectral reflectance, and wherein plural speckle statistics are derived including at least a speckle contrast and a speckle patch size.

12. The method according to claim 1, wherein a probability distribution function of the identity of the illuminated material is determined based at least in part on the comparison, wherein each candidate material identity is associated with a probability.

13. The method according to claim 10, wherein deriving the spectral characteristic comprises spectral analysis of the light reflected from the illuminated material.

14. The method according to claim 13, wherein the light source which emits light of controlled coherence properties comprises a laser light source, and wherein spectral analysis includes capture of light reflected from the illuminated material with a spectral sensor.

15. The method according to claim 13, wherein the one or more light sources include multiple coherent light sources, each comprised of a laser with a respectively different wavelength, and wherein spectral analysis includes capture of light reflected from the illuminated material with a spectral sensor.

16. The method according to claim 13, wherein the one or more light sources include at least one incoherent light in conjunction with a laser light source, and wherein spectral analysis includes capture of light reflected from the illuminated material with a spectral sensor.

17. The method according to any one of claim 15 or 16, wherein the light sources are applied simultaneously.

18. The method according to any one of claim 15 or 16, wherein the light sources are applied sequentially.

19. The method according to claim 10, wherein the spectral characteristic includes spectral reflectance, and wherein plural speckle statistics are derived including at least a speckle contrast and a speckle patch size.

20. The method according to claim 10, wherein a probability distribution function of the identity of the illuminated material is determined based at least in part on the comparison, wherein each candidate material identity is associated with a probability.

* * * * *